United States Patent
Journot et al.

(10) Patent No.: US 10,112,042 B2
(45) Date of Patent: Oct. 30, 2018

(54) APPARATUS AND METHODS FOR TISSUE ANCHORING OF MEDICAL DEVICES

(71) Applicant: MEDTRONIC, INC., Minneapolis, MN (US)

(72) Inventors: Brice J. Journot, Osseo, MN (US); Daniel C. Oster, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 347 days.

(21) Appl. No.: 14/964,265

(22) Filed: Dec. 9, 2015

(65) Prior Publication Data

US 2016/0166279 A1    Jun. 16, 2016

Related U.S. Application Data (60) Provisional application No. 62/090,431, filed on Dec. 11, 2014.

(51) Int. Cl.
| | |
|---|---|
| *A61M 25/02* | (2006.01) |
| *A61N 1/05* | (2006.01) |
| *A61N 1/00* | (2006.01) |
| *A61B 17/34* | (2006.01) |
| *A61F 2/848* | (2013.01) |

(52) U.S. Cl.
CPC ............ *A61N 1/05* (2013.01); *A61B 17/3462* (2013.01); *A61M 25/02* (2013.01); *A61N 1/00* (2013.01); *A61B 2017/347* (2013.01); *A61B 2017/3484* (2013.01); *A61F 2/848* (2013.01)

(58) Field of Classification Search
CPC ........ A61B 2017/347; A61B 2017/348; A61B 2017/3482; A61B 2017/3484; A61B 2017/3488; A61F 2/848; A61F 2220/0008; A61F 2220/0016; A61M 2025/0233; A61M 2025/024; A61M 2025/0286; A61M 25/02; A61M 25/04; A61N 1/05; A61N 1/0502; A61N 1/0504; A61N 1/057; A61N 1/059; A61N 2001/058

See application file for complete search history.

(56) References Cited

U.S. PATENT DOCUMENTS 4,453,292 A * 6/1984 Bakker ................ F16G 11/101
                                                      24/115 G
4,553,961 A * 11/1985 Pohndorf .............. A61B 17/04
                                                      604/175

(Continued)

*Primary Examiner* — Ryan J Severson
(74) *Attorney, Agent, or Firm* — Withers & Keys, LLC (57) ABSTRACT

An apparatus for tissue anchoring of a medical device includes a retention member and an elastic member secured between ends of the retention member. The retention member, being transformable along a longitudinal axis of the apparatus, is held by a spring bias of the elastic member in a first, gripping state; and, when opposing forces compress the elastic member, the retention member is transformed to a second, open state. In the first state, a lumen defined by a sidewall of the retention member has a diameter to forms a interference fit around a body of the device, and the ends of the retention member are spaced apart by a first distance; in the second state, the ends are spaced closer together than in the first state, and the diameter of the lumen is enlarged to allow movement of the apparatus along a length of the device body.

26 Claims, 9 Drawing Sheets

(56) References Cited

U.S. PATENT DOCUMENTS

| | | | | |
|---|---|---|---|---|
| 5,152,298 | A * | 10/1992 | Kreyenhagen | A61B 17/0401 604/175 |
| 5,197,166 | A * | 3/1993 | Meier | F16G 11/101 24/115 G |
| 5,257,975 | A * | 11/1993 | Foshee | A61B 17/34 604/105 |
| 5,476,493 | A * | 12/1995 | Muff | A61N 1/057 604/175 |
| 6,473,654 | B1 * | 10/2002 | Chinn | A61N 1/05 600/375 |
| 7,398,125 | B2 * | 7/2008 | Osypka | A61N 1/057 604/174 |
| 7,831,313 | B2 * | 11/2010 | Lauro | A61N 1/05 24/136 R |
| 7,875,056 | B2 * | 1/2011 | Jervis | A61B 17/0487 24/115 M |
| 7,899,553 | B2 * | 3/2011 | Barker | A61N 1/0558 600/375 |
| 8,229,573 | B2 | 7/2012 | Chen | |
| 8,467,883 | B2 * | 6/2013 | Chen | A61N 1/0558 600/386 |
| 9,352,147 | B2 * | 5/2016 | Nguyen-Stella | A61N 1/0558 |
| 2007/0050005 | A1 * | 3/2007 | Lauro | A61N 1/05 607/126 |
| 2008/0243220 | A1 * | 10/2008 | Barker | A61N 1/0558 607/126 |
| 2011/0022141 | A1 * | 1/2011 | Chen | A61N 1/0558 607/117 |
| 2016/0166279 | A1 * | 6/2016 | Journot | A61N 1/00 606/108 |

* cited by examiner

FIGURE 5B

APPARATUS AND METHODS FOR TISSUE ANCHORING OF MEDICAL DEVICES

TECHNICAL FIELD

The present disclosure is related to implantable medical devices, and more particularly to apparatus and methods for tissue anchoring of elongate bodies of the devices.

BACKGROUND

Figure 1:
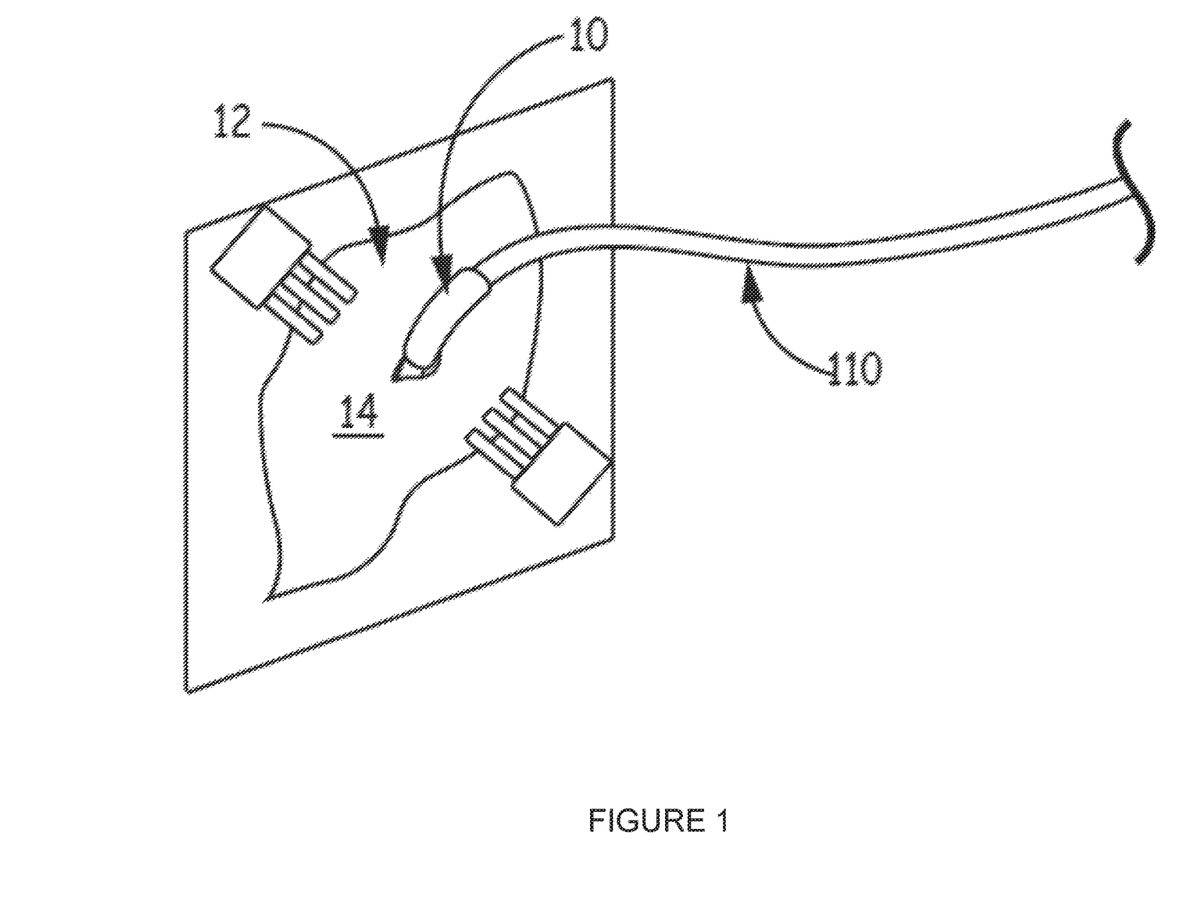
FIG. 1 is a schematic depicting a surgical incision site through which an exemplary elongate medical device has been implanted.

A variety of elongate medical device bodies, for example, drug delivery catheters and medical electrical leads, are known in the art, for example, to couple a therapy delivery generator and/or diagnostic device to a target site within a body of a patient, for example, in the spinal column or in any of a number of internal organs. Those skilled in the art are familiar with various apparatus and methods for anchoring these implanted device bodies. FIG. 1 is a schematic depicting a surgical incision site 12 through which an exemplary elongate medical device body 110 has been implanted. FIG. 1 illustrates a length of device body 110 extending proximally out from site 12, and an anchor apparatus 10 surrounding device body 110 to facilitate anchoring of device body 110 to subcutaneous tissue 14, for example, via sutures (not shown) tied thereabout and sewn into the tissue 14. Anchor apparatus 10, for example, configured as a silicone sleeve, can provide a protective interface between sutures and device body 110, when the sutures are secured around device body 110 to prevent movement of body 110 relative to both apparatus 10 and the tissue anchoring site. However it may be preferable that an anchor apparatus be configured to provide a uniform, even compression around body 110, which prevents movement of body 110 relative to the anchor apparatus, without the sutures. Tools for deploying such an anchor apparatus onto device bodies are known in the art, yet there is still a need for new apparatus and methods for tissue anchoring of medical devices.

BRIEF DESCRIPTION OF THE DRAWINGS

The following drawings are illustrative of particular embodiments and do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of inventive embodiments disclosed herein in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 2A:
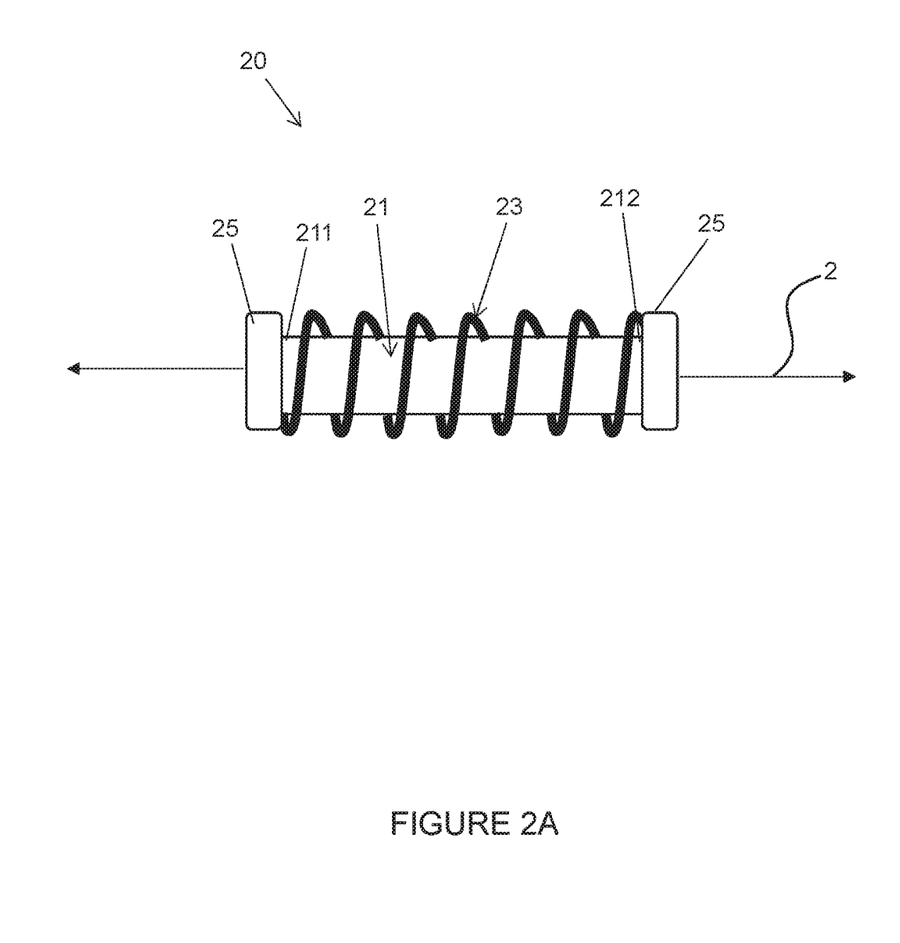
FIG. 2A is a plan view of an exemplary apparatus for tissue anchoring, according to some embodiments.

FIG. 2A is a plan view of an exemplary apparatus 20 for tissue anchoring, according to some embodiments. FIG. 2A illustrates apparatus 20 including a retention member 21, an elastic member 23, and a pair of force interface members 25, wherein elastic member is secured between first and second ends 211, 212 of retention member 21 and each force interface member 25 is coupled in proximity to one of the first and second ends 211, 212. FIG. 2A further illustrates apparatus 20 having a longitudinal axis 2 along which retention member 21 extends. According to the illustrated embodiment, elastic member 23, which is shown as a coiled spring, is spring biased to push first and second ends 211, 212 apart from one another, thereby holding retention member 21 in a first, gripping state.

Figure 2B:
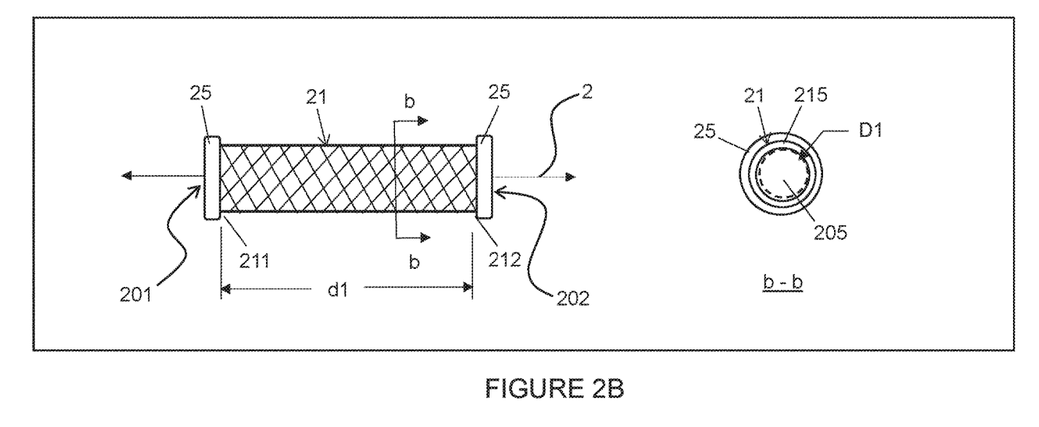
FIG. 2B is a plan view and corresponding end view of a portion of the apparatus of FIG. 2A in a first, gripping state, according to some embodiments.
Figure 2C:
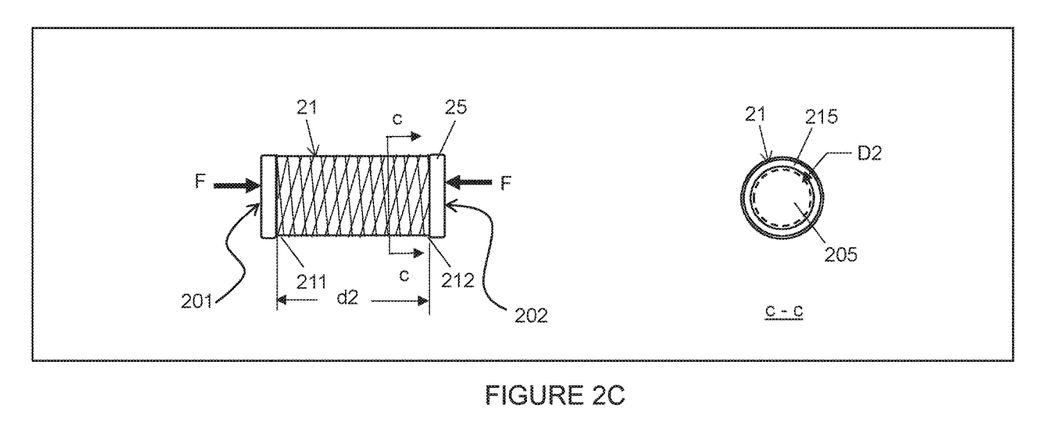
FIG. 2C is a plan view and corresponding end view of a portion of the apparatus of FIG. 2A in a second, open state, according to some embodiments.

FIG. 2B is a plan view and corresponding end view of apparatus 20, from which elastic member 23 is removed for simplicity of illustration, with retention member 21 in the first, gripping state. FIG. 2B illustrates a tubular sidewall 215 of retention member 21 defining a lumen 205 of retention member 21, wherein lumen 205 extends along axis 2 from a first opening 201 thereof to a second opening 202 thereof. FIG. 2B further illustrates first and second ends 211, 212 of retention member 21 being spaced apart by a first distance d1, which corresponds to lumen 205 having a first diameter D1 to form an interference fit around an implantable device body, for example, device body 110 (FIG. 1), in order to grip the device body for tissue anchoring. FIG. 2C is a plan view and corresponding end view of apparatus 20 with retention member in a second, open state, at which the implantable device body may be inserted within apparatus 20 so that apparatus may be positioned along a length thereof, for example, along device body 110 in lieu of anchor sleeve 10 (FIG. 1). According to the illustrated embodiment, when opposing forces F are applied to force interface members 25 to compress elastic member 23 (FIG. 2A) against the spring bias thereof, retention member 21 is transformed to the second, open state, at which first and second ends 211, 212 are spaced apart by a second distance d2, which is less than first distance d1, and lumen 205 is enlarged from first diameter D1 to a second diameter D2, which is greater than an outer diameter of the aforementioned device body.

According to an exemplary embodiment, tubular sidewall 215 of retention member 21 is formed by a plurality of braided medical grade polymer strands for example, selected from, but not limited to, polyester, nylon, Polyether ether ketone (PEEK), Polytetrafluoroethylene (PTFE), High density polyethylene (HDPE), and the like, wherein the braided nature of sidewall 215 allows retention member 21 to be transformable between the first, gripping state, at which the braid is hyperextended, and the second, open state, at which the braid is compressed. In some embodiments, retention member 21 further includes a liner, which is shown with dashed lines in the end views of FIGS. 2B-C, wherein the liner conforms to the changing diameter of lumen 205, and may be a coating applied to an inner surface of tubular sidewall 215, or a separate tubing mounted within sidewall 215, or a series of bands spaced apart around a perimeter of lumen 205, mounted within sidewall 215, any of which may be formed from silicone rubber, which provides a relatively tacky interface with the device body. Thus, the optional liner can increase a coefficient of friction between apparatus 20 and the body, when retention member 21 is in the first, gripping state. With reference back to FIG. 2A, elastic member 23 may be formed from a coiled metallic wire, for example, medical grade titanium, Nitinol, or stainless steel or any other suitable medical grade alloy, or a plastic coil may be employed for elastic member 23, for example, medical grade HDPE, PEEK or nylon, or even a polymer tube spring. The spring bias of elastic member 23, or any of the other elastic members disclosed below, will adjust over time, as the braid of sidewall 215 may stress elongate and relax under tension, to help maintain a consistent level of retention for retention member 21.

According to some embodiments, apparatus 20 may be constructed by joining first and second ends 211, 212 of retention member 21 to force interface members 25 (and ends of the liner, if included and in the form of the tubing or bands), for example, by insert molding of interface members 25 around ends of tubular sidewall 215, and/or by crimping methods, and/or by adhesive bonding methods, and/or ultrasonic welding methods known in the art, when interface members are formed from a compatible plastic material, such as HDPE, PEEK, nylon, or PTFE, and by securing ends of elastic member 23 between force interface members 25, for example, by a mechanical interlocking, which may be formed by crimping or during insert molding, and/or by adhesive bonding or ultrasonic welding if materials are compatible. Alternately, it is contemplated that an elastic member, like the coiled spring, may be integrated into tubular wall 215 of retention member 21, for example, being woven into the aforementioned braided strands thereof.

Figure 2D:
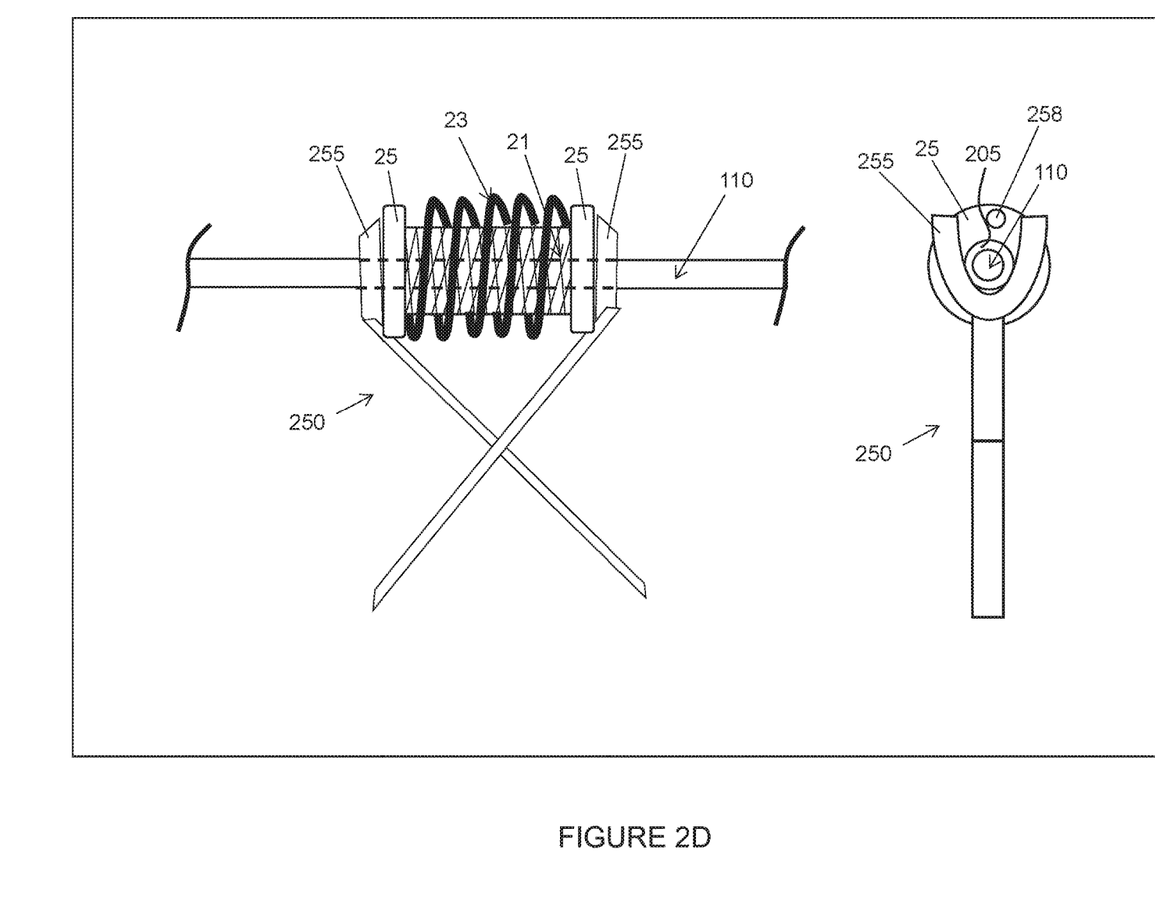
FIG. 2D is a schematic elevation and associated end view of the apparatus of FIGS. 2A-C along with a tool that engages the apparatus, according to some embodiments.

FIG. 2D is a schematic elevation and associated end view of apparatus 20 along with a forceps-like tool 250 that engages force interface members 25 of apparatus 20, according to some methods and embodiments. FIG. 2D illustrates engaged opposing jaws 255 of tool 250 applying the above-described opposing forces to compress elastic member 23 against the spring bias thereof and thereby transform retention member 21 of apparatus 20 into the second, open state for insertion of device body 110 through lumen 205. Thus, apparatus 20 may be positioned along a length of device 110 with forceps-like tool 250, which may be included together with apparatus 20 in a kit, according to some embodiments.

With further reference to FIG. 2D, each jaw 255 is configured to provide clearance for passage of device body 110 into lumen 205. According to some methods, after an operator employs tool 250 to position apparatus 20 at a desired location along device body 110, for example, between layers of subcutaneous tissue, and then releases jaws 255 of tool 250 from engagement with force interface members 25, the spring bias of elastic member 23 transforms retention member 21 back to the first, gripping state to grip body 110 with the aforementioned relatively tight interference fit thereabout, which prevents movement of device body 110 relative to apparatus 20 when apparatus 20 anchors device body to the tissue, for example, completed by sutures sewn through a tissue fixation member of apparatus 20, such as loops or apertures thereof, for example, an aperture 258, which is shown formed in force interface member 25 (end view of FIG. 2D). Alternately, sutures can be sewn through gaps between segments of elastic member 23 and retention member 21, but, in alternate embodiments of apparatus for tissue anchoring, for example, as described below in conjunction with FIGS. 4, 5A-B, 6A-B, and 8, tissue fixation members are included so that suturing may not be necessary.

Figure 3A:
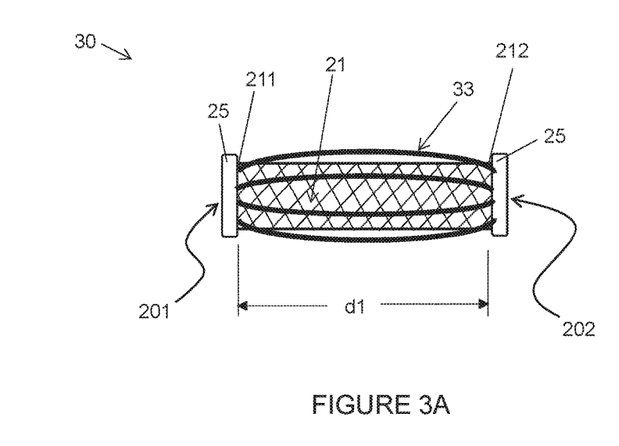
FIG. 3A is a plan view of an exemplary apparatus for tissue anchoring, according to some alternate embodiments, in a first, gripping state.
Figure 3B:
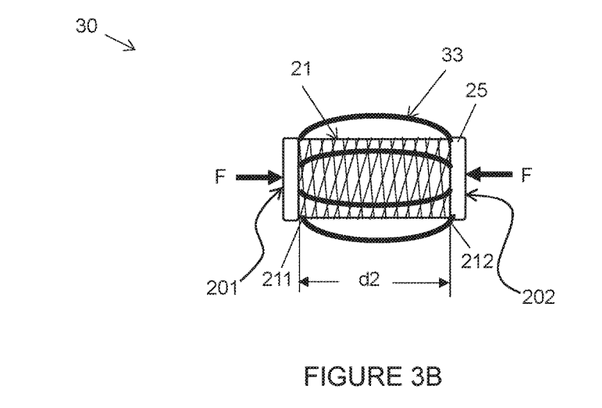
FIG. 3B is a plan view of the exemplary apparatus of FIG. 3A in a second, open state, according to some embodiments.

FIGS. 3A-B are plan views of an exemplary apparatus 30 for tissue anchoring, according to some alternate embodiments, wherein an elastic member thereof is formed by a multi-beam, or leaf spring element 33. FIG. 3A illustrates apparatus 30 in a first, gripping state, at which a spring-bias of leaf spring element 33 pushes first and second ends 211, 212 of retention member 21 apart; and FIG. 3B illustrates apparatus 30 in a second, open state, at which opposing forces F are applied to force interface members 25 to compress leaf spring element 33, against the spring bias thereof. FIGS. 3A-B further illustrate the first and second distances d1, d2 at which first and second ends 211, 212 are spaced from one another in the first state and second state, respectively, similar to apparatus 20; and like apparatus 20, lumen 205 has first and second diameters D1, D2 as described above. According to some exemplary embodiments, leaf spring element 33 is constructed from any the aforementioned medical grade metal alloys or plastics that can form elastic member 23, and may be assembled into apparatus 30 by securing ends of element 33 between force interface members 25, according to the methods mentioned above for elastic member 23.

Figure 4:
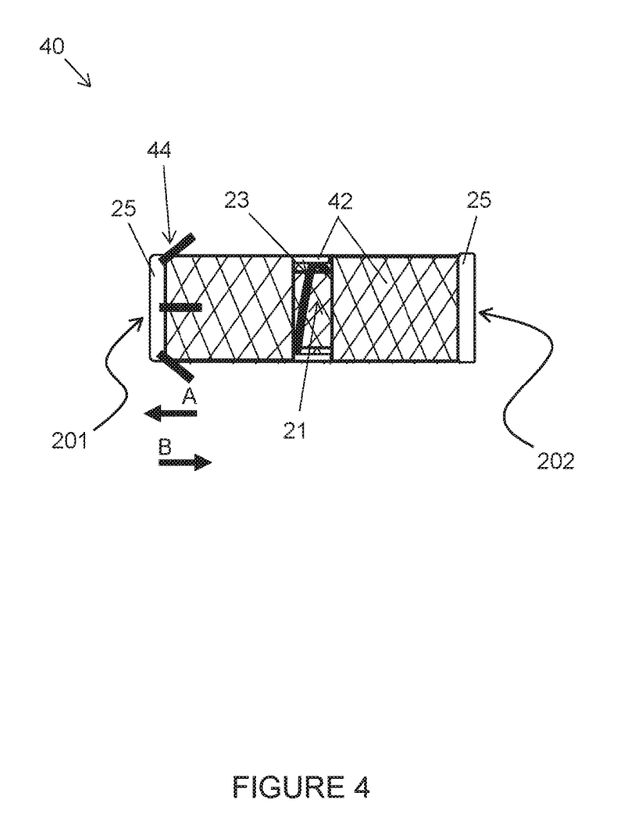
FIG. 4 is a plan view, with a partial cut-away section, of another exemplary apparatus for tissue anchoring, according to some additional embodiments.

FIG. 4 is a plan view, with a partial cut-away section, of another exemplary apparatus 40 for tissue anchoring, according to some additional embodiments. FIG. 4 illustrates apparatus 40 including retention member 21, elastic member 23 (or elastic member 33 could be substituted for member 23), and force interface members 25, similar to apparatus 20, and further including an optional outer sheath 42 (partial cut-away section), and a tissue fixation member formed by a flexible tine element 44. Optional outer sheath 42 is shown extending between interface members 25 and around elastic member 23, and may be formed by a plurality of braided medical grade polymer strands, similar to retention member 21, or formed by an elastic polymer tube, for example, a silicone rubber tube. In some embodiments, optional outer sheath 42 includes tine-like elements (not shown) protruding therefrom and oriented like the tines of tine element 44, to provide additional tissue fixation, if outer sheath 42 is included. In alternate embodiments, tine element 44 need not be included if sheath 42 with tine elements is included. According to the illustrated embodiment, when an operator applies the above-described opposing forces and moves apparatus 40 in a first direction, per arrow A, to position apparatus 40 along a length of a medical device body, for example, as described above for apparatus 20 and device body 110 (FIG. 2D), the tines of tine element 44 (and/or the tine-like elements of sheath 42) are collapsed, or pushed down toward sheath 42, by surrounding layers of tissue; then, once the operator has positioned apparatus 40 at a desired location along the length of the device body, and releases the opposing forces to transform retention member 21 to the first, gripping state, the operator can pull back on the gripped device body, per arrow B, so that ends of the tines catch in the surrounding tissue for fixation of apparatus 40. According to an exemplary embodiment, flexible tine element 44 is a separate component, for example, formed from a medical grade hard plastic or metal, which is mechanically interlocked with and/or bonded to one of force interface members 25; alternately, tine element 44 may be integrally formed in the interface member 25.

Figure 5A:
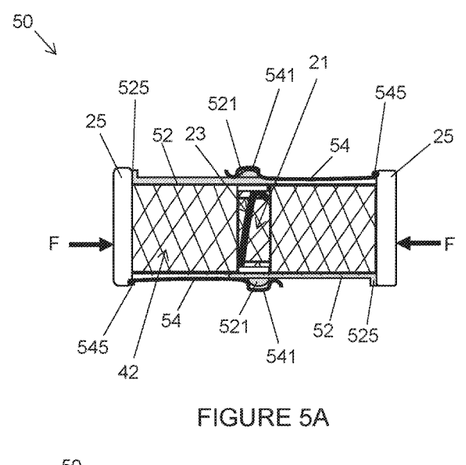
FIG. 5A is a plan view, with a partial cut-away section, of another exemplary apparatus for tissue anchoring, according to some embodiments, in a second, open state.
Figure 5B:
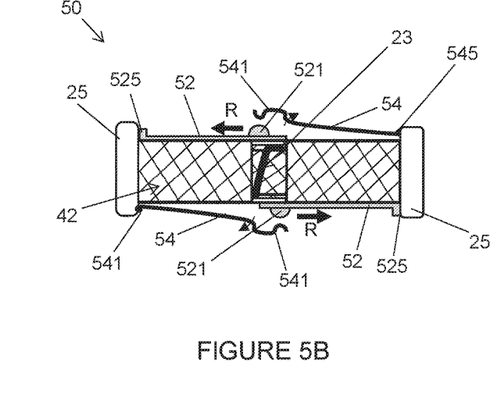
FIG. 5B is another plan view of the apparatus of FIG. 5A in a first, gripping state, according to some embodiments.

FIGS. 5A-B are plan views, each with a partial cut-away section, of another exemplary apparatus 50 for tissue anchoring, according to some embodiments. FIGS. 5A-B illustrate apparatus 50 including retention member 21, elastic member 23 (alternately, elastic member 33), force interface members 25, and outer sheath 42, like the embodiments described above, and further including deployment members 52 and a tissue fixation member formed by deployable tine or barb elements 54. FIGS. 5A-B further illustrate each barb or tine element 54 including a fixed end 545 and free end 541, and each deployment member 52 including an outward protruding ramp member 521. An end 525 of each deployment member 52 is shown secured to a corresponding force interface member 25, for example, by an insert molding process, and/or by adhesive bonding and/or ultrasonic welding methods known in the art; but, a remainder of each deployment member 52 is free to slide relative to outer sheath 42 as apparatus 50 is transformed between the first and second states, as described below. Deployment members 52 may be formed from a medical grade hard plastic, for example, any of the exemplary materials presented above for members 25.

According to the illustrated embodiment, when opposing forces F hold elastic member 23 of apparatus 50 against the spring bias thereof so that retention member 21 is in the second, open state, as illustrated in FIG. 5A, each tine or barb element 54 is un-deployed. Thus, apparatus 50, with tine or barb elements 54 un-deployed has a relatively low profile so that an operator can insert apparatus 50 between layers of tissue when positioning apparatus 50 along a length of an implanted medical device body as described above. Then, with reference to FIG. 5B, when the operator removes the opposing forces F to release elastic member 23, the spring bias of the elastic member not only transforms retention member 21 to the first, gripping state, as described above, but also moves ramp members 521 of deployment members 52, per arrows R, via secured ends 525 thereof, so that ramp members 521 force free ends 541 of each tine or barb element 54 outward to engage with tissue surrounding the implanted device body. According to some exemplary embodiments, and tine or barb elements 54 are formed from a relatively hard medical grade plastic or metal, which may be joined to interface members 25 via insert molding or bonding/welding in combination with an interlocking fit. Some embodiments are contemplated in which fixed ends 545 of tine or barb elements 54 are spring loaded to bias free ends 541 outward, thus, free ends 541 are configured to interlock with ramp members 521 in the second, open state (FIG. 5A).

Figure 6A:
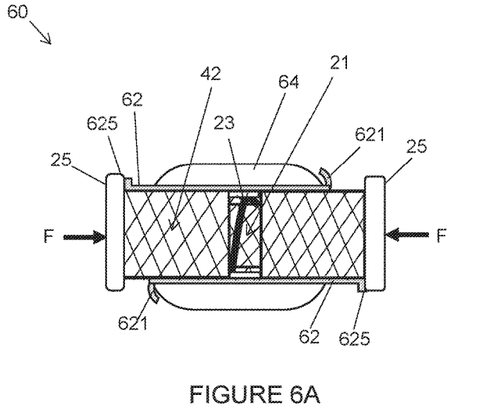
FIG. 6A is a plan view, with a partial cut-away section, of another exemplary apparatus for tissue anchoring, according to some additional embodiments, in a second, open state.
Figure 6B:
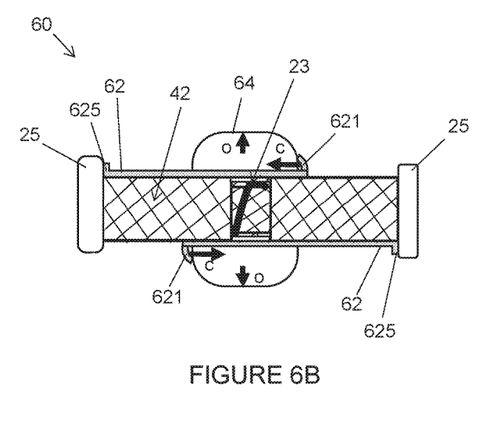
FIG. 6B is another plan view of the apparatus of FIG. 6A in a first, gripping state, according to some embodiments.

FIGS. 6A-B are plan views, each with a partial cut-away section, of another exemplary apparatus 60 for tissue anchoring, according to some additional embodiments. FIGS. 6A-B illustrate apparatus 60 including retention member 21, elastic member 23 (alternately, elastic member 33), force interface members 25, and outer sheath 42, like the embodiments described above, and further including deployment members 62 and a tissue fixation member, which is formed by an expandable element 64 and mounted around deployment members 62 and between outward protruding tabs 621 thereof. FIGS. 6A-B further illustrate each deployment member 62 including an end 625 secured to a corresponding force interface member 25, for example, by an insert molding process, and/or by adhesive bonding and/or ultrasonic welding methods known in the art; but, a remainder of each deployment member 62 is free to slide relative to outer sheath 42 as apparatus 60 is transformed between the first and second states, as described below.

According to the illustrated embodiment, when opposing forces F hold elastic member 23 of apparatus 60 against the spring bias thereof so that retention member 21 is in the second, open state, as illustrated in FIG. 6A, expandable element 64 is un-deployed, having a relatively low profile, so that an operator can insert apparatus 60 between layers of tissue when positioning apparatus 60 along a length of an implanted medical device body as described above. Then, with reference to FIG. 6B, when the operator removes the opposing forces F to release elastic member 23, the spring bias of elastic member 23 not only transforms retention member 21 to the first, gripping state, as described above, but also moves tabs 621 of deployment members 62 closer together, per arrows c, via secured ends 625 thereof, to compress expandable element 64 and thereby open up element 64, per arrows o, to a larger fixation profile for engaging with tissue surrounding the implanted device body. According to some exemplary embodiments, expandable element 64 is a tubular member formed from a plurality of braided fibers, for example, similar to an embodiment of retention member 21 described above, that 'bunches up' when compressed between tabs 621 of sheath 62. Alternately, expandable element 64 may be formed by a flexible polymer, such as medical grade silicone rubber. In either case, tabs 621 of deployment members 62 may be fixedly attached to opposing sides of expandable element 64, according to some embodiments.

Figure 7:
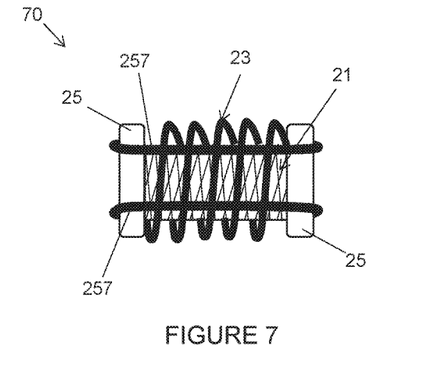
FIG. 7 is a plan view of another exemplary apparatus for tissue anchoring, according to further embodiments.

FIG. 7 is a plan view of another exemplary apparatus 70 for tissue anchoring, according to further embodiments. FIG. 7 illustrates apparatus 70 including all the components described above for apparatus 20 (FIG. 2A), namely retention member 21, elastic member 23, and force interface members 25. However, apparatus 70 further includes one or more removable bands 257 secured around force interface members 25 to apply the opposing forces that compress elastic member 23 against the spring bias thereof, and thereby transform apparatus 70 to the second, open state, as shown in FIG. 7. Once an operator has positioned apparatus 70, with retention member 21 thereof in the second, open state, along a length of a medical device body, the operator can simply remove band(s) 257 to release the opposing forces, so that elastic member 23, according to the spring bias thereof, transforms retention member 21 to the first, gripping state. Removable band(s) 257 may be formed from a relatively stiff plastic, for example, a medical grade nylon material.

Figure 8:
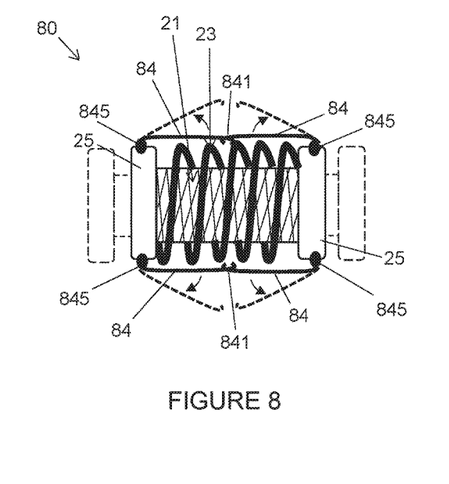
FIG. 8 is a plan view of yet another exemplary apparatus for tissue anchoring, according to yet further embodiments.

FIG. 8 is a plan view of yet another exemplary apparatus 80 for tissue anchoring, according to yet further embodiments. FIG. 8 illustrates apparatus 80 including all the components described above for apparatus 20 (FIG. 2A), namely retention member 21, elastic member 23, and force interface members 25. However, apparatus 80 further includes one or more pairs of deployable tine or barb elements 84 and a corresponding separable coupling 841 for each pair, wherein each separable coupling 841 is formed between free ends of opposing tine or barb elements 84, as shown in FIG. 8. FIG. 8 further illustrates each tine or barb element 84 including a fixed end joined at a corresponding junction 845 of the corresponding force interface member 25, which may be a spring loaded junction 845 to facilitate the deployment of tine or barb elements 84 described below.

According to the illustrated embodiment, opposing forces that compress elastic member 23 against the spring bias thereof, to transform retention member 21 to the second, open state, as shown, are applied through opposing junctions 845 of each pair of tine or barb elements 84, when the free ends thereof are coupled together by separable coupling 841. Once an operator has positioned apparatus 80, with retention member 21 thereof in the second, open state, along a length of a medical device body, the operator can simply detach each separable coupling 841 to deploy the free ends of tine or barb elements 84 (shown with dashed lines in FIG. 8), which releases the opposing forces so that elastic member 23, according to the spring bias thereof, transforms retention member 21 to the first, gripping state (also shown with dashed lines). Thus, in the first, gripping state, apparatus 80 not only grips around the device body but is also secured to surrounding tissue by engagement therewith by the deployed tine or barb elements 84. Elements 84 may be formed from a relatively hard medical grade plastic or metal.

In the foregoing detailed description, the invention has been described with reference to specific embodiments. However, it may be appreciated that various modifications and changes can be made without departing from the scope of the invention as set forth in the appended claims. Furthermore various combinations of elements described above in conjunction with the specific embodiments, are within the scope of the present invention.

The invention claimed is:

1. An apparatus for tissue anchoring of an elongate medical device body, the apparatus comprising:
   a retention member including a tubular sidewall that extends from a first end of the retention member to a second end of the retention member and defines a lumen of the retention member, the lumen extending along a longitudinal axis of the apparatus from a first opening thereof to a second opening thereof, and the retention member being transformable along the longitudinal axis from a first, gripping state to a second, open state, and vice versa, the first state being that at which the lumen has a first diameter and the first and second ends of the tubular sidewall are spaced apart by a first distance, and the second state being that at which the lumen has a second diameter and the first and second ends of the tubular sidewall are spaced apart by a second distance, the first diameter being smaller than the second diameter, and the first distance being greater than the second distance;
   an elastic member secured between the first and second ends of the retention member, the elastic member being spring biased to push the first and second ends apart from one another, thereby holding the retention member in the first, gripping state;
   a pair of force interface members, a first of the pair of interface members being coupled to the retention member in proximity to the first end thereof, a second of the pair of interface members being coupled to the retention member in proximity to the second end thereof, and the interface members being configured to receive opposing forces that compress the elastic member, against the spring bias thereof, and thereby transform the retention member to the second, open state; and
   a flexible tissue fixation member directed outward from the retention member, when the retention member is in the first, gripping state;
   wherein the apparatus is positionable along a length of the medical device body when the retention member is in the second, open state, and grips the medical device body when the retention member is in the first, gripping state.

2. The apparatus of claim 1, wherein the tubular sidewall of the retention member comprises a plurality of strands braided together.

3. The apparatus of claim 1, wherein the retention member further comprises a liner extending within the tubular sidewall and around the lumen.

4. The apparatus of claim 1, wherein the elastic member comprises a coiled spring mounted around the tubular sidewall of the retention member, outside the lumen.

5. The apparatus of claim 1, wherein the elastic member comprises a leaf spring element mounted alongside the tubular sidewall of the retention member, outside the lumen.

6. The apparatus of claim 1, wherein the tissue fixation member comprises a flexible tine element coupled in proximity to one of the first and second ends of the tubular sidewall of the retention member.

7. The apparatus of claim 1, further comprising an outer sheath extending between the force interface members and around the elastic member.

8. The apparatus of claim 7, further comprising a deployment member extending alongside the outer sheath and being free to slide relative to the sheath, and wherein:
   the deployment member includes an end secured to the first force interface member and an outward protruding ramp member spaced apart, along the longitudinal axis, from the secured end; and
   the tissue fixation member comprises a deployable tine or barb element, the tine or barb element including a fixed end and a free end, the fixed end coupled to the second force interface member, and the free end configured to engage with the ramp member of the deployment member; and
   when the opposing forces that compress the elastic member are released, the ramp member of the deployment member forces the free end of the tine or barb element outward from the longitudinal axis to engage tissue.

9. The apparatus of claim 7, further comprising a pair of deployment members extending alongside the outer sheath and being free to slide relative to the outer sheath, and wherein:
   each deployment member includes an end secured to a corresponding force interface member, and an outward protruding tab spaced apart, along the longitudinal axis, from the secured end, the tabs of the pair of deployment members being located closer together, along the longitudinal axis, when the retention member is in the first, gripping state, than when the retention member is in the second, open state; and
   the tissue fixation member comprises an expandable element mounted around the pair of deployment members and between the outward protruding tabs thereof, the expandable element having a relatively low profile, when the retention member is in the second, open state, and the expandable element having a larger, fixation profile, when the retention member is in the first, gripping state, being compressed by the outward protruding tabs of the deployment members.

10. The apparatus of claim 1, wherein:
the tissue fixation member comprises a pair of deployable tine or barb elements and a separable coupling, each deployable tine or barb element including a fixed end and a free end, and the separable coupling engaging and thereby holding the free ends of the pair of deployable tine or barb elements together so that the pair of elements are in an un-deployed state;
each force interface member includes a junction that joins the fixed end of the corresponding tine or barb element to the interface member, so that the opposing forces that compress the elastic member, against the spring bias thereof, are applied through each junction by the holding together of the free ends of the pair of deployable tine or barb elements by the separable coupling; and
when the separable coupling for the pair of deployable tine or barb elements is detached, the free ends of the pair of deployable tine or barb elements are deployed and the opposing forces are released to allow the retention member to transform to the first, gripping state.

11. The apparatus of claim 1, further comprising at least one removable band secured around the pair of force interface members to apply the opposing forces that compress the elastic member.

12. A kit comprising an apparatus for tissue anchoring of an elongate medical device body, and an associated tool configured to engage with the apparatus and thereby facilitate positioning of the apparatus along a length of the device body, and wherein the apparatus comprises:
a retention member including a tubular sidewall that extends from a first end of the retention member to a second end of the retention member and defines a lumen of the retention member, the lumen extending along a longitudinal axis of the apparatus from a first opening thereof to a second opening thereof, and the retention member being transformable along the longitudinal axis from a first, gripping state to a second, open state, and vice versa, the first state being that at which the lumen has a first diameter and the first and second ends of the tubular sidewall are spaced apart by a first distance, and the second state being that at which the lumen has a second diameter and the first and second ends of the tubular sidewall are spaced apart by a second distance, the first diameter being smaller than the second diameter, and the first distance being greater than the second distance;
an elastic member secured between the first and second ends of the retention member, the elastic member being spring biased to push the first and second ends apart from one another, thereby holding the retention member in the first, gripping state;
a pair of force interface members, a first of the pair of interface members being coupled to the retention member in proximity to the first end thereof, a second of the pair of interface members being coupled to the retention member in proximity to the second end thereof, and the interface members being configured to receive opposing forces that compress the elastic member, against the spring bias thereof, and thereby transform the retention member to the second, open state; and
a flexible tissue fixation member directed outward from the retention member, when the retention member is in the first, gripping state;

wherein, when the tool engages the apparatus force interface members, the apparatus, with the retention member thereof in the second, open state, is positionable along the length of the device body; and
when the tool is released from engagement with the apparatus force interface members, the apparatus, with the retention member thereof in the first, gripping state, grips the medical device body.

13. The kit of claim 12, wherein the tubular sidewall of the apparatus retention member comprises a plurality of strands braided together.

14. The kit of claim 12, wherein the apparatus retention member further comprises a liner extending within the tubular sidewall and around the lumen.

15. The kit of claim 12, wherein the apparatus elastic member comprises a coiled spring mounted around the tubular sidewall of the apparatus retention member, outside the lumen.

16. The kit of claim 12, wherein the elastic member comprises a leaf spring element mounted alongside the tubular sidewall of the apparatus retention member, outside the lumen of the retention member.

17. The kit of claim 12, wherein the apparatus tissue fixation member comprises a flexible tine element coupled in proximity to one of the first and second ends of the tubular sidewall of the apparatus retention member.

18. The kit of claim 12, wherein the apparatus further comprises an outer sheath extending between the apparatus force interface members and around the apparatus elastic member.

19. The kit of claim 18, wherein:
the apparatus further comprises a deployment member extending alongside the outer sheath of the apparatus and being free to slide relative to the sheath;
the deployment member includes an end secured to the first force interface member of the apparatus and an outward protruding ramp member spaced apart, along the longitudinal axis of the apparatus, from the secured end;
the tissue fixation member of the apparatus comprises a deployable tine or barb element, the tine or barb element including a fixed end and a free end, the fixed end coupled to the second force interface member of the apparatus, and the free end configured to engage with the ramp member of the deployment member; and
when the opposing forces that compress the elastic member of the apparatus are released, the ramp member of the deployment member forces the free end of the tine or barb element outward from the longitudinal axis to engage tissue.

20. The kit of claim 18, wherein:
the apparatus further comprises a pair of deployment members extending alongside the outer sheath of the apparatus and being free to slide relative to the outer sheath;
each deployment member includes an end secured to a corresponding force interface member of the apparatus, and an outward protruding tab spaced apart, along the longitudinal axis, from the secured end, the tabs of the pair of deployment members being located closer together, along the longitudinal axis of the apparatus, when the retention member of the apparatus is in the first, gripping state, than when the retention member is in the second, open state; and
the tissue fixation member of the apparatus comprises an expandable element mounted around the pair of deployment members and between the outward protruding tabs thereof, the expandable element having a relatively low profile, when the retention member is in the second, open state, and the expandable element having a larger, fixation profile, when the retention member is in the first, gripping state, being compressed by the outward protruding tabs of the deployment members.

21. A method for securing an anchoring apparatus around an elongate body of a medical device, the method comprising:
providing the anchoring apparatus, the anchoring apparatus comprising:
a retention member including a tubular sidewall that extends from a first end of the retention member to a second end of the retention member and defines a lumen of the retention member, the lumen extending along a longitudinal axis of the apparatus from a first opening thereof to a second opening thereof, and the retention member being transformable along the longitudinal axis from a first, gripping state to a second, open state, and vice versa, the first state being that at which the lumen has a first diameter and the first and second ends of the tubular sidewall are spaced apart by a first distance, and the second state being that at which the lumen has a second diameter and the first and second ends of the tubular sidewall are spaced apart by a second distance, the first diameter being smaller than the second diameter, and the first distance being greater than the second distance,
an elastic member secured between the first and second ends of the retention member, the elastic member being spring biased to push the first and second ends apart from one another, thereby holding the retention member in the first, gripping state,
a pair of force interface members, a first of the pair of interface members being coupled to the retention member in proximity to the first end thereof, a second of the pair of interface members being coupled to the retention member in proximity to the second end thereof, and the interface members being configured to receive opposing forces that compress the elastic member, against the spring bias thereof, and thereby transform the retention member to the second, open state, and
a flexible tissue fixation member directed outward from the retention member, when the retention member is in the first, gripping state, wherein the apparatus is positionable along a length of the medical device body when the retention member is in the second, open state, and grips the medical device body when the retention member is in the first, gripping state;
applying opposing forces to compress the elastic member of the apparatus against a spring bias of the elastic member and thereby transform the retention member from the first state to the second state;
inserting the body of the device through the lumen of the apparatus while applying the opposing forces; and
releasing the opposing forces to allow the retention member to transform back to the first state, at which the retention member grips the device body.

22. The method of claim 21, wherein:
applying the opposing forces comprises engaging a forceps-like tool with the pair of force interface members of the apparatus; and
releasing the opposing forces comprises disengaging the forceps-like tool from the pair of force interface members of the apparatus.

23. The method of claim 21, wherein:
applying the opposing forces comprises forming a separable coupling to attach together free ends of a pair of deployable tine or barb elements of the apparatus, a first tine or barb element of the pair being joined to the apparatus in proximity to the first end thereof, and a second tine or barb element of the pair being joined to the apparatus in proximity to the second end thereof; and
releasing the opposing forces comprises detaching the separable coupling.

24. The method of claim 21, wherein:
applying the opposing forces comprises securing a removable band to a pair of force interface members of the apparatus, a first force interface member of the pair being located at the first end of the apparatus, and a second force interface member of the pair being located at the second end of the apparatus; and
releasing the opposing forces comprises removing the removable band.

25. An apparatus for tissue anchoring of an elongate medical device body, the apparatus comprising:
a retention member including a tubular sidewall that extends from a first end of the retention member to a second end of the retention member and defines a lumen of the retention member, the lumen extending along a longitudinal axis of the apparatus from a first opening thereof to a second opening thereof, and the retention member being transformable along the longitudinal axis from a first, gripping state to a second, open state, and vice versa, the first state being that at which the lumen has a first diameter and the first and second ends of the tubular sidewall are spaced apart by a first distance, and the second state being that at which the lumen has a second diameter and the first and second ends of the tubular sidewall are spaced apart by a second distance, the first diameter being smaller than the second diameter, and the first distance being greater than the second distance;
an elastic member secured between the first and second ends of the retention member, the elastic member being spring biased to push the first and second ends apart from one another, thereby holding the retention member in the first, gripping state;
a pair of force interface members, a first of the pair of interface members being coupled to the retention member in proximity to the first end thereof, a second of the pair of interface members being coupled to the retention member in proximity to the second end thereof, and the interface members being configured to receive opposing forces that compress the elastic member, against the spring bias thereof, and thereby transform the retention member to the second, open state; and
a tissue fixation member directed outward from the retention member, when the retention member is in the first, gripping state; wherein the apparatus is positionable along a length of the medical device body when the retention member is in the second, open state, and grips the medical device body when the retention member is in the first, gripping state;
an outer sheath extending between the force interface members and around the elastic member;

a deployment member extending alongside the outer sheath and being free to slide relative to the sheath, and wherein:

the deployment member includes an end secured to the first force interface member and an outward protruding ramp member spaced apart, along the longitudinal axis, from the secured end; and the tissue fixation member comprises a deployable tine or barb element, the tine or barb element including a fixed end and a free end, the fixed end coupled to the second force interface member, and the free end configured to engage with the ramp member of the deployment member; and when the opposing forces that compress the elastic member are released, the ramp member of the deployment member forces the free end of the tine or barb element outward from the longitudinal axis to engage tissue.

26. A kit comprising an apparatus for tissue anchoring of an elongate medical device body, and an associated tool configured to engage with the apparatus and thereby facilitate positioning of the apparatus along a length of the device body, and wherein the apparatus comprises:

a retention member including a tubular sidewall that extends from a first end of the retention member to a second end of the retention member and defines a lumen of the retention member, the lumen extending along a longitudinal axis of the apparatus from a first opening thereof to a second opening thereof, and the retention member being transformable along the longitudinal axis from a first, gripping state to a second, open state, and vice versa, the first state being that at which the lumen has a first diameter and the first and second ends of the tubular sidewall are spaced apart by a first distance, and the second state being that at which the lumen has a second diameter and the first and second ends of the tubular sidewall are spaced apart by a second distance, the first diameter being smaller than the second diameter, and the first distance being greater than the second distance;

an elastic member secured between the first and second ends of the retention member, the elastic member being spring biased to push the first and second ends apart from one another, thereby holding the retention member in the first, gripping state;

a pair of force interface members, a first of the pair of interface members being coupled to the retention member in proximity to the first end thereof, a second of the pair of interface members being coupled to the retention member in proximity to the second end thereof, and the interface members being configured to receive opposing forces that compress the elastic member, against the spring bias thereof, and thereby transform the retention member to the second, open state; and a tissue fixation member directed outward from the retention member, when the retention member is in the first, gripping state;

wherein, when the tool engages the apparatus force interface members, the apparatus, with the retention member thereof in the second, open state, is positionable along the length of the device body; and when the tool is released from engagement with the apparatus force interface members, the apparatus, with the retention member thereof in the first, gripping state, grips the medical device body;

wherein the apparatus further comprises an outer sheath extending between the apparatus force interface members and around the apparatus elastic member;

the apparatus further comprises a deployment member extending alongside the outer sheath of the apparatus and being free to slide relative to the sheath;

the deployment member includes an end secured to the first force interface member of the apparatus and an outward protruding ramp member spaced apart, along the longitudinal axis of the apparatus, from the secured end;

the tissue fixation member of the apparatus comprises a deployable tine or barb element, the tine or barb element including a fixed end and a free end, the fixed end coupled to the second force interface member of the apparatus, and the free end configured to engage with the ramp member of the deployment member; and when the opposing forces that compress the elastic member of the apparatus are released, the ramp member of the deployment member forces the free end of the tine or barb element outward from the longitudinal axis to engage tissue.

* * * * *